(12) United States Patent
Hughes et al.

(10) Patent No.: US 6,863,843 B2
(45) Date of Patent: Mar. 8, 2005

(54) NAPHTHOPYRAN COMPOUNDS, PHOTORESPONSIVE COMPOSITIONS AND LENSES

(75) Inventors: Frank J. Hughes, Edina, MN (US); Xuzhi Qin, Hacienda Heights, CA (US); J. Thomas Ippoliti, St. Paul, MN (US)

(73) Assignee: Vision-Ease Lens, Inc., Ramsey, MN (US)

(*) Notice: Subject to any disclaimer, the term of this patent is extended or adjusted under 35 U.S.C. 154(b) by 319 days.

(21) Appl. No.: 09/746,322

(22) Filed: Dec. 21, 2000

(65) Prior Publication Data

US 2002/0080451 A1 Jun. 27, 2002

(51) Int. Cl.[7] .............................................. G02B 5/23
(52) U.S. Cl. .................... 252/586; 351/163; 549/389; 548/525
(58) Field of Search .................. 252/586; 351/163; 549/389; 548/525

(56) References Cited

U.S. PATENT DOCUMENTS

| | | | |
|---|---|---|---|
| 3,567,605 A | | 3/1971 | Becker |
| 3,627,690 A | | 12/1971 | Casella et al. |
| 4,818,096 A | | 4/1989 | Heller et al. |
| 5,066,818 A | | 11/1991 | Gemert et al. |
| 5,349,065 A | * | 9/1994 | Tanaka ..................... 252/586 |
| 5,888,432 A | | 3/1999 | Chan |
| 5,955,520 A | | 9/1999 | Heller et al. |
| 6,197,225 B1 | * | 3/2001 | Tanizawa .................. 252/586 |

FOREIGN PATENT DOCUMENTS

| | | |
|---|---|---|
| GB | 2146327 | 4/1985 |
| GB | 2190379 | 11/1987 |
| JP | 08-295690 | * 11/1996 |
| WO | 98/42695 | * 10/1998 |

* cited by examiner

*Primary Examiner*—Philip C. Tucker
(74) *Attorney, Agent, or Firm*—Mark A. Litman & Associates, P.A.

(57) ABSTRACT

A photochromic [1,2-b] naphthopyran having a fluoro substituent in at least one of the 7-position or the 9-position of the naphthopyran provides a stable photochromic compound with a narrow range of absorption. A preferred photochromic naphthopyran has the 2-position of the naphthopyran with two aromatic substituents thereon. It is further preferred to have at least one 2-position aromatic substituent comprising a phenyl group. The photochromic naphthopyran may also have at least one 2-position aromatic substituent comprise a phenyl group having one substituent selected from the group consisting of an anthranilyl, azepinyl, benzoxazolyl, dialkylamino, diazepinyl, diazolyl, imidazolidinyl, imidazolyl, imidazolinyl, indazolyl, indoeninyl, indolinyl, indolizinyl, indolyl, indoxazinyl, isobenzazolyl, isoindolyl, isooxazolyl, isooxazyl, isopyrrol, isoquinolyl, isothiazolyl, julolideno, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinocyclidinyl, quinolyl, thiazolyl, triazolyl and triazyl group.

3 Claims, 7 Drawing Sheets

NAPHTHOPYRAN COMPOUNDS, PHOTORESPONSIVE COMPOSITIONS AND LENSES

BACKGROUND OF THE INVENTION

1. Field of the Invention

The present invention relates to the field of photoreactive or photoresponsive dyes, particularly photochromic dyes that change their absorbance characteristics in response to ambient radiation conditions. The invention also relates to the use of such photoresponsive dyes in compositions, coatings, layers and lenses, particularly ophthalmic lenses (both prescription and piano lenses).

2. Background of the Art

Conventional commercial photoreactive lenses, i.e. lenses that darken in sunlight and lighten again in the shade, are manufactured from glass and utilize the reversible formation of silver particles from dispersed silver halide salts to bring about the darkening of the lenses.

Plastic lenses have advantages over glass; principally they are lighter in weight (particularly in the case of ophthalmic lenses having high powers) and less prone to breakage. Since the above described action of dispersed silver salts does not take place in plastics matrices, attempts have been made to develop photochromic compounds which would produce the same kind of effect in plastics materials. The ideal compound for this purpose should, when absorbed or coated on a conventional plastics lens, possess the following properties i.e., a high quantum yield for coloring in the near ultra-violet, a low quantum yield for bleaching with visible light, and a fast thermal fade at ambient temperatures.

Unfortunately, these properties are also generally associated with thermal or photochemical instability so that the useful life of sunglasses incorporating such compounds would be too short for commercial feasibility.

U.S. Pat. No. 3,567,605 (Becker) describes a series of pyran derivatives, including certain benzopyrans and naphthopyrans, but not spiro-compounds, which exhibit photochromic properties. These compounds can be regarded as derivatives of chromene. Typically, the compounds undergo a colorless to yellow-orange change on irradiation by U.V. light. However, the observation of this behavior by Becker was restricted to temperatures below about −40° C. and Becker reported that the color change was reversed when the temperature was raised to a temperature in the range of −10° C. to 0° C.

Padwa et al in J. Org. Chem., vol. 40, No. 8, 1975, page 1142, examined the photochemical reactions of compounds of the kind described by Becker, identified the by-products and suggested pathways to ring-opened colored intermediates and the final non-colored phenolics. The colored forms examined by Padwa were unstable at room temperature, at which temperature he suggested that the colored quinonealide intermediates either thermally revert to the starting material or undergo 1,4 addition of the methanol solvent to form the corresponding phenolic ether product or a 1,5-hydrogen shift in acetone to form the corresponding phenol. However, Padwa does not suggest ways in which the stability of the compounds he examined might be improved nor any modification which might be made to the structure of known pyran compounds in order to induce photoreactive behavior in a plastics lens.

The required properties of a photochromic compound for sunglasses application are outlined above and compounds which possess these properties have been termed "heliochromic" compounds in U.K. Pat. No. 2146327. Thus, the term "heliochromic" compound is used in this specification to mean a compound which possesses the following properties, namely (a) a high quantum efficiency for coloring in the near ultra-violet, (b) a low quantum yield for bleaching with visible white light and (c) a fast thermal fade at ambient temperature but not so rapid that the combination of white light bleaching and thermal fade prevent coloring by the U.V. component of strong sunlight. Such properties make the compound eminently suitable for use in photoreactive lenses.

In U.K. Patent Applications Nos. 86/11837 and 87/050, 101, there is described a series of pholochromic adamantane spiropyrans which possess the above-described desirable heliochromic properties, in conjunction with good thermal and photo-chemical stability. These adarlantane spiropyrans can also be incorporated into standard plastics lens materials, such as CR39 by imbibition and members of this series have been shown to be capable of undergoing a large number of cycles without significant degradation. It has been described that the reason why these compounds exhibit these improved properties is that in accordance with Bredt's rule, the spiro-carbon cannot become doubly-bonded and therefore the ring-opened colored form is resistant to degradations associated with 1,5-hydrogen shift.

However, one limitation of the compounds of this series is that the compounds which show the best resistance towards degradation exhibit a color change on exposure to a U.V. light (or sunlight) from colorless to yellow/orange. The market demand is, however, largely for lenses that darken to brown or gray. The above applications indicate that a photoreactive lens can be produced by incorporating a blend of a yellow and a blue photochromic compound into the lens. In practice, however, it has proved difficult to prepare purple/blue coloring photochromic compounds whose resistance to degradation or fatigue is equivalent to that of the best of the yellow coloring adamantine spiropyrans.

U.S. Pat. No. 4,818,096 describes photoreactive lenses with adamantine spiro compounds in which a mixture of photoreactive dyes is used to overcome the deficiencies of the individual dyes, In particular, this Patent describes the use of a combination of a) an admantine 2-spiro-benzopyran or 2-spiro-naphthopyran and b) a blue coloring photochromic benzopyran or naphthopyran having a nitrogen-containing substituent in the 2-position of the pyran ring. The combination of the yellow/orange coloring admantine 2-spiro pyran compound and the purple/blue coloring pyran provides a desired brown/gray coloration in the darkened areas. The blue coloring pyrans having the nitrogen-containing substituent in the 2-position are described a s novel where the 2-position substituent comprises a phenyl group having an amino or substituted amino or nitrogen-containing heterocylic substituent in the ortho-position or para-position of the phenyl group. These novel dyes were shown in the lenses only in combination with the yellow/orange coloring dyes. The invention touts the ability of the unique structure of the dye in providing a double maximum absorption from the dye, one absorbing at about 590 nm and the other absorbing at 500 nm and below to provide a purple/blue coloring pyran.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrams and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in this patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-o]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho- or para- positions.

U.S. Pat. No. 5,888,432 describes that the presence of an adamantyl group in position 2 of naphtho- or benzopyrans allowed lowering the lambda-max of the colored form. These types of molecules adapt well in association with blue and/or violet and/or red complementary photochromes to give gray or brown tints. Those benzopyran derivatives are substituted in position 2 with an adamantyl group, itself optionally substituted with at least one linear or branched alkyl group that comprises from 1 to 6 carbon atoms. Advantageously, the adamantyl group is linked in position 1. The carbon in position 2 of the benzopyran derivatives (the carbon which carries therefore the adamantyl group and advantageously the adamant-1-yl group) is an asymmetric carbon. In the context that invention, the carbon, in position 2, in addition to the adamantyl group, bears a second substituent group S. These 2-adamantyl-2-S benzopyrans have particularly interesting photochromic properties.

U.S. Pat. No. 5,955,520 describes photochromic indeno-fused naphthopyrans in which an indeno ring group is fused to the f-side of the naphtha portion of a naphthopyran, and having specific substituents at the 3-position of the naphthopyran. A list of acceptable 3-position substituents for the practice of that invention is provided in detail on columns 3–5 of this patent reference, which patent is incorporated herein by reference for the totality of that disclosure. The data shows, for the very limited number of examples evaluated in Table II, the dyes with two $\lambda_{max}$ absorption peaks (e.g., Dye 1, $\lambda_{max}$=425 (minor), 536 (major); and Dye CE1, $\lambda_{max}$=407 (minor), 482 (major)).

In accordance with the invention of U.S. Pat. No. 5,955,520, certain novel 1H-indeno-2,1-f-naphtho[1,2-b]-pyrans having activated colors ranging from orange to blue/gray, an acceptable fade rate, high activated intensity and a high coloration rate may be prepared. These compounds may be described as indeno fused [1,2-b]-naphthopyrans having certain substituents at the 3 position of the pyran ring. Certain substituents may also be present at the number 5, 6, 7, 8, 9, 10, 11, 12, or 13 carbon atoms of the compounds There is a continuing need for novel photoreactive or photochromic dyes and compositions that can provide different chromic and physical properties.

BRIEF DESCRIPTION OF THE INVENTION

Certain novel naphthopyran compounds described by formulae herein have been found to be highly efficient photoreactive dyes that when exposed to electromagnetic radiation containing ultraviolet rays, such as the ultraviolet radiation in sunlight or the light of a mercury lamp, exhibit a reversible change in color. When the ultraviolet radiation is discontinued, such a photochromic compound will return to its original color or colorless state. These compounds are stable, reversibly bleach quickly, and provide a blue color within a very desirable region of the electromagnetic spectrum. The photochromic compounds find applications in various fields, for example for the manufacture of ophthalmic lenses, contact lenses, solar protection lenses, filters, camera optical systems or photographic apparatus optical systems or optical systems of other optical devices, and observation optical systems, glazings, decorative objects, bill elements or even for the storage of information by optical inscription (coding). The present invention relates to novel substituted naphthopyran compounds that have a naphtho portion with one or more fluoro or other halogen and/or a methoxy substitutions. These compounds, in addition to the requirements described above, may have certain particularly beneficial substituents at the 3-position of the pyran ring. These particular compounds have unexpectedly been found to demonstrate a bathochromic shift for the wavelength in the visible spectrum at which the maximum absorption of the activated (colored) form of the photochromic compound, i.e., the lambda max (visible), occurs, thereby resulting in activated colors ranging from orange to blue/gray. In addition, these compounds have demonstrated a high molar absorptivity (or molar extinction coefficient) in the UV, an acceptable fade rate without the addition of acids or bases, a highly activated intensity, a controlled double absorption, and a high coloration rate.

The naphthopyran compounds of the present invention possess at least a 7-fluoro or 9-fluoro substituent on the naphtho group of the naphthopyran. Other substituent contributions for physical purposes of stability, bathachromic shift, solubility, fade rate, coloration rate, and the like may also be included, but the essential characteristics of the specifically desired range of blue absorption, with an essentially narrow, single range for $\lambda_{max}$ wavelength absorption are provided by the unique substitution on the compounds of the present invention.

Reference to the following chemical formula and the definition of the respective groups on that formula will assist in the understanding of the present invention. It is to be noted that, except for the requirement of at least one 7-fluoro, 7-methoxy, 9-methoxy and/or 9-fluoro substituent, all other substitutions shown on the naphthopyran are exemplary and not limiting, unless otherwise stated. In Formula 1, a generic structural formula for the photochromic naphthopyrans of the present invention is shown with substituents $R_1$, $R_2$, $R_5$, $R_6$, $R_7$, $R_8$, $R_9$, $R_{10}$, referred to herein as the "general R groups" while $R_7$ and $R_9$ are referred to as the "specifically fluoro-substituted groups."

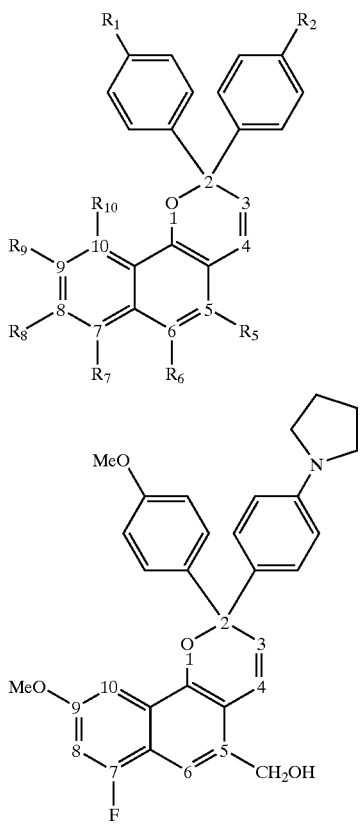

In this formula of one preferred embodiment of the present invention, $R_1$ is shown as a methoxy group, $R_2$ is shown as a pyrrolidino group, $R_5$ is shown as a methylol group, $R_7$ is a fluoro group, and $R_9$ is a methoxy group. Additional substitution may be present on positions on the group, such as those positions ortho- and meta- to the $R_1$ and $R_2$ groups. Similarly, some substitution is known in the art to be tolerable on the 3- and 4-positions shown in these formulae. Additionally, within the broad class of [1,2-b]-naphthopyrans of the invention, the 2-position may be substituted with a polynuclear group with two arms of one of the ring nuclei bonded to the 2-position, such as a fluorene attached through the available position on the five-membered central nucleus (the 9-position of the fluorene group). Similarly, an anthracene group, xanthene, and the like may be bonded to the 2-position of the benzopyran.

DETAILED DESCRIPTION OF THE INVENTION

Figure 1A:
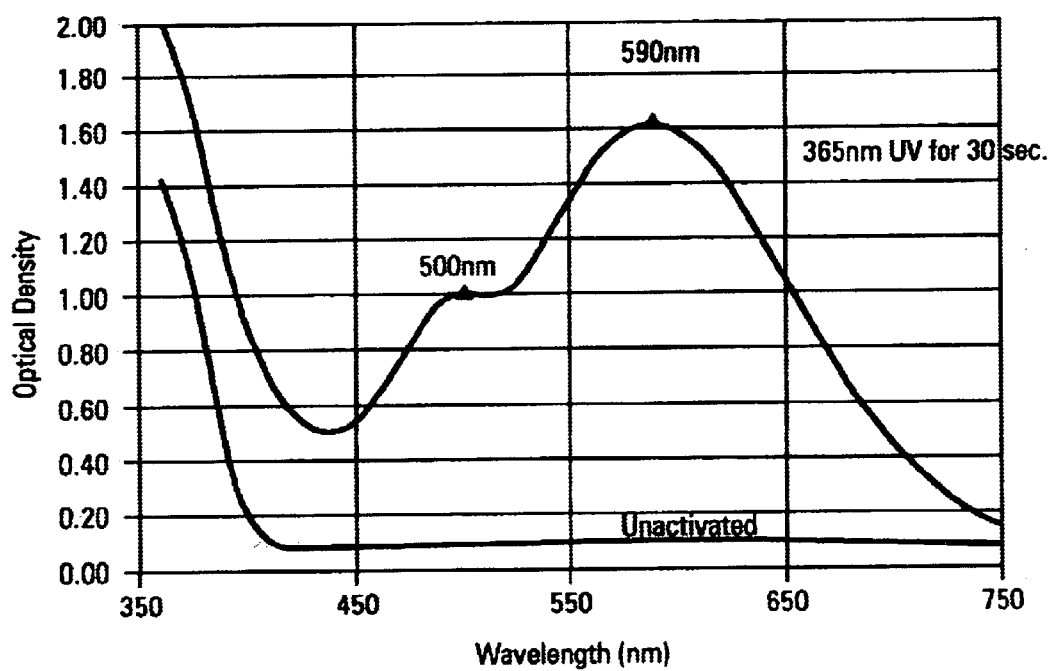
FIG. 1a shows the activation profile of a naphthopyran photochromic dye of the prior art represented by U.S. Pat. No. 4,818,096.
Figure 1B:
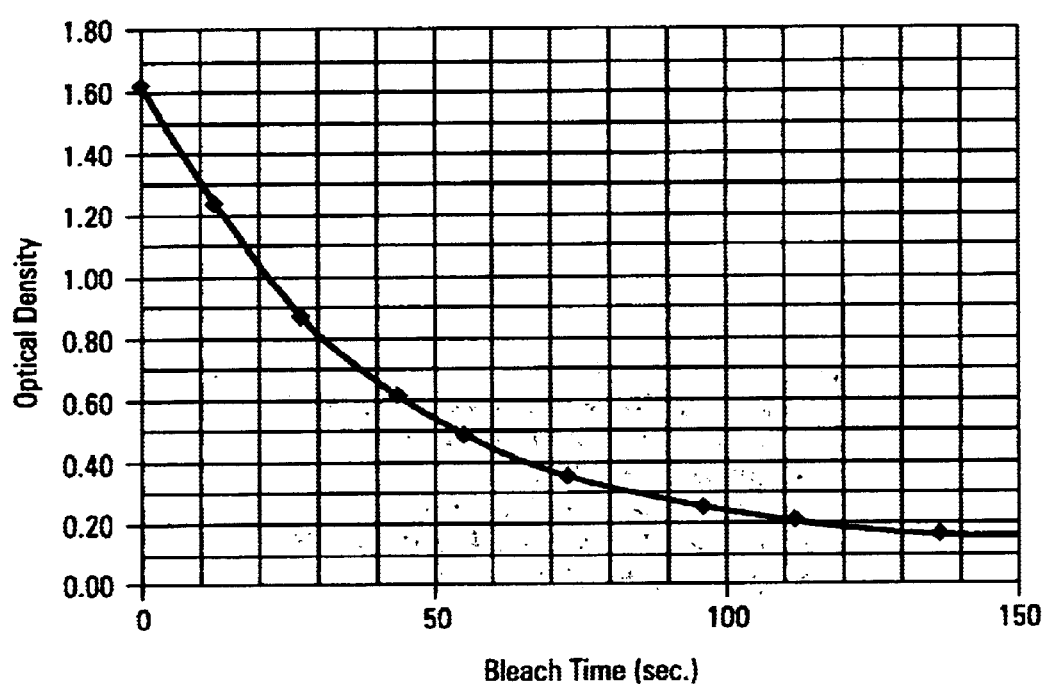
FIG. 1b shows the natural bleaching profile of a naphthopyran photochromic dye of the prior art represented by U.S. Pat. No. 4,818,096.
Figure 2A:
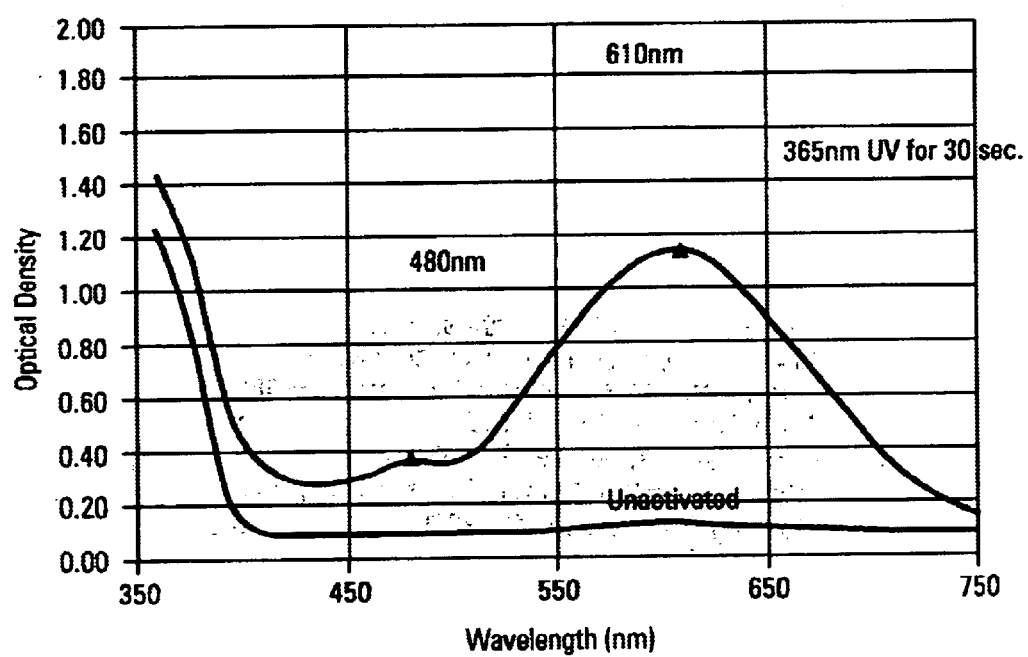
FIG. 2a shows the activation profile of a naphthopyran photochromic dye of the present invention.
Figure 2B:
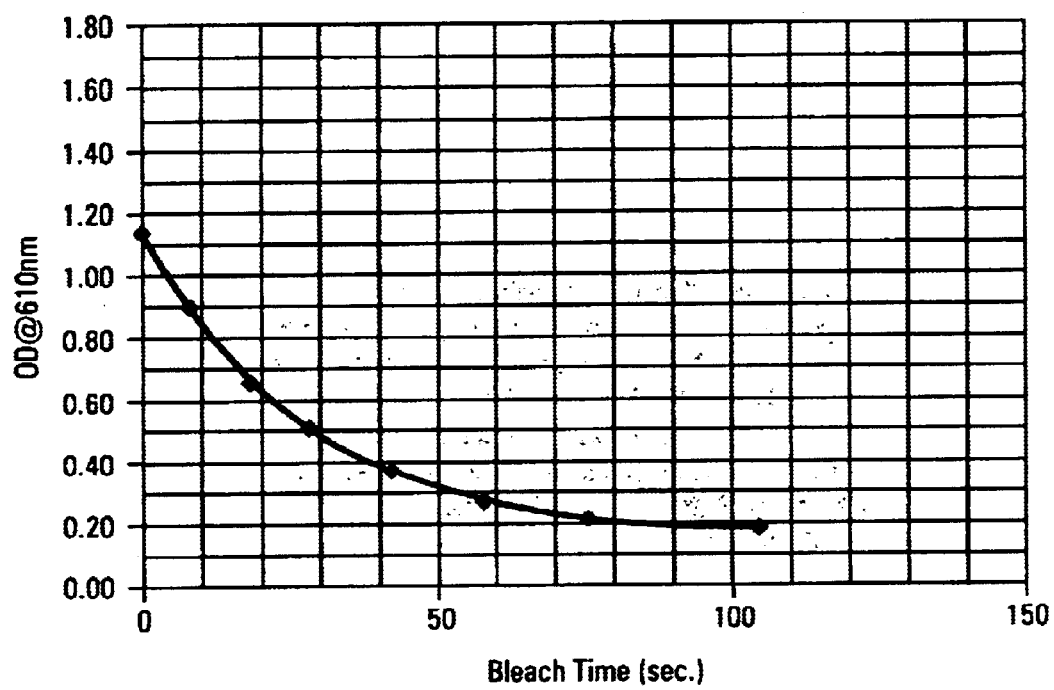
FIG. 2b shows the natural bleaching profile of a naphthopyran photochromic dye of the present invention.
Figure 3A:
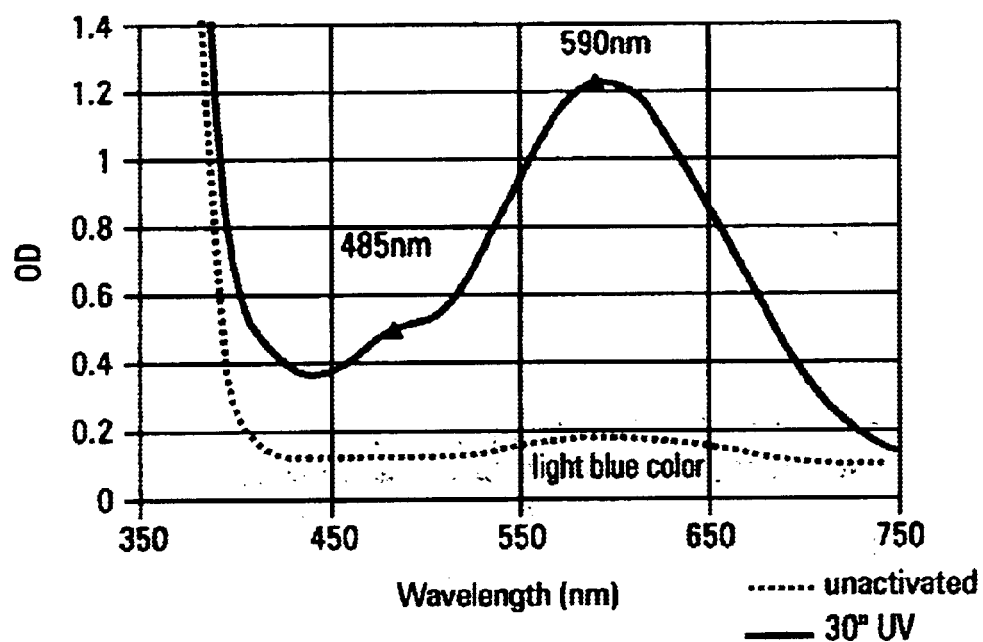
FIG. 3a shows the activation profile of a naphthopyran photochromic dye of the present invention.
Figure 3A:
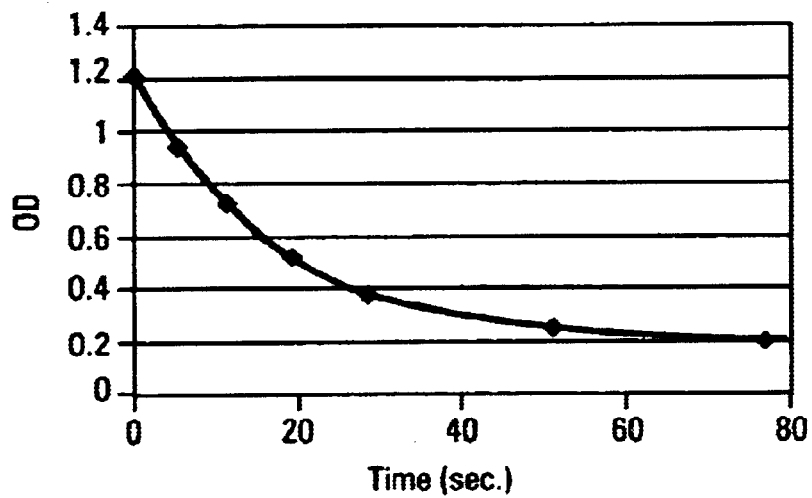
Figure 3B:
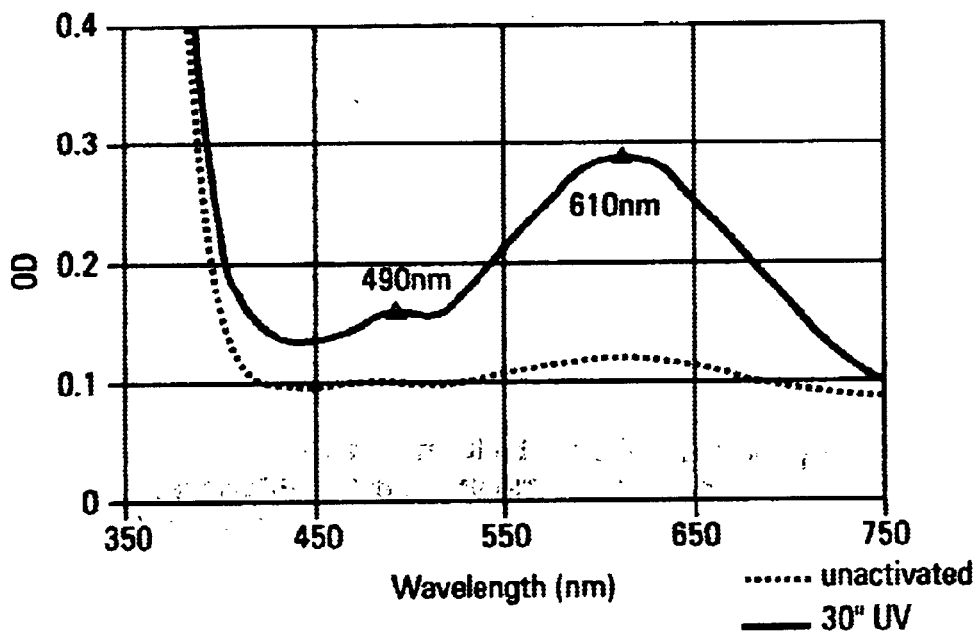
FIG. 3b shows the activation profile of a naphthopyran photochromic dye of the present invention.
Figure 3B:
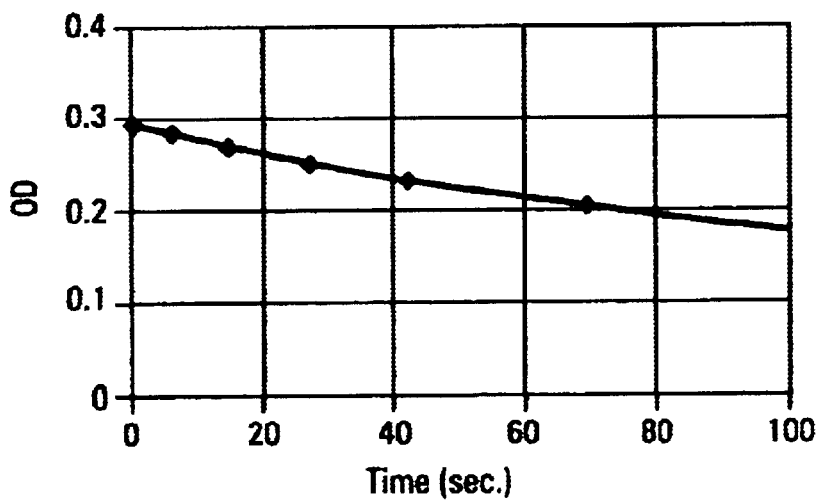
Figure 3C:
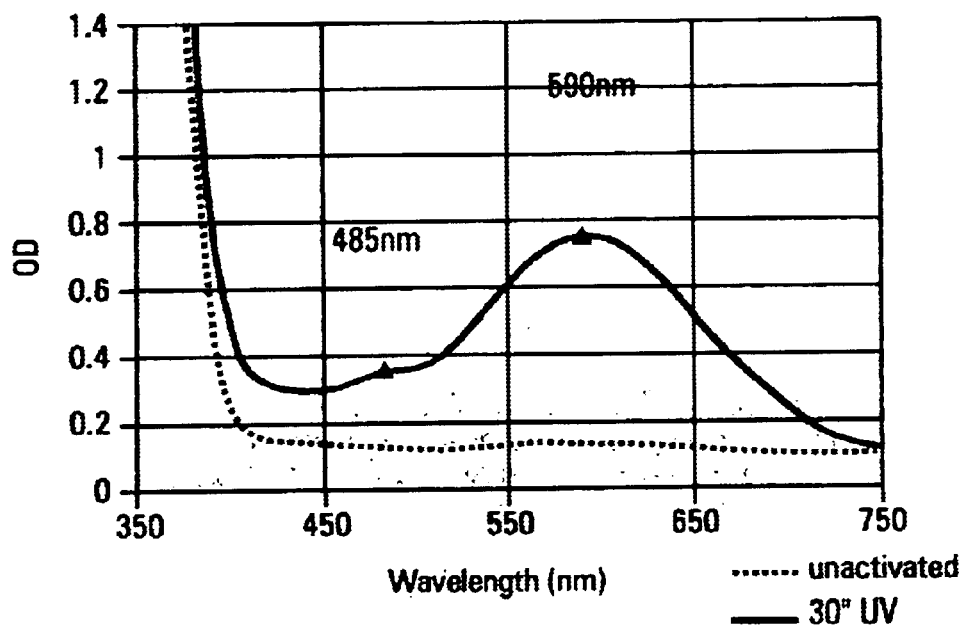
FIG. 3c shows the activation profile of a naphthopyran photochromic dye of the present invention.
Figure 3C:
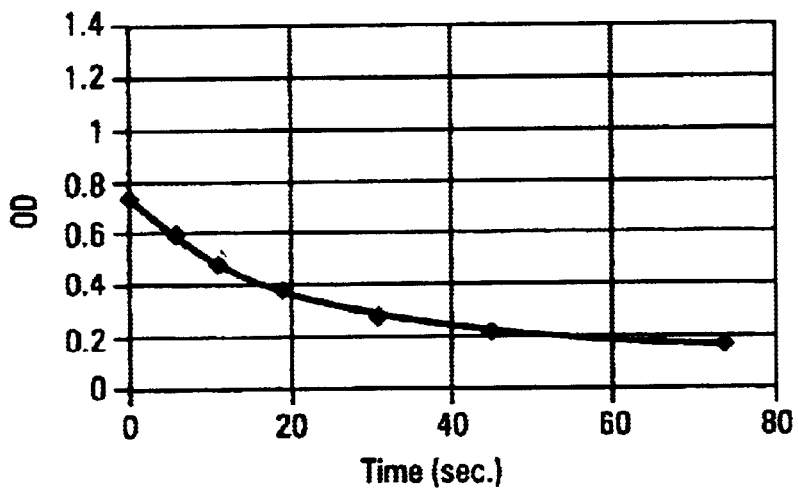

The present invention relates to certain novel naphthopyran compounds. More particularly, this invention relates to novel photochromic naphthopyran compounds having a naphtho portion with one or more fluoro or other halogen and/or a methoxy substituents and to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

An important aspect of the performance of photochromic compounds is the ability to provide both types of rapid response rates (both for coloration when light radiation increases and decloration when light intensity decreases), sufficient color density upon activation to effect light absorption, and design acceptable color balance. When substitutions on naphthopyran photochromic compounds are made for one specific effect (e.g., increasing response rates), the substituent may and often does have effects on other performance attributes that are undesirable. As noted in U.S. Pat. No. 4,818,096, the unique blends of substituents described therein may provide (see FIG. 5 and Example 12) a double maximum absorption curve for activated photochromic naphthopyrans. The present invention has found a particular type of substitution on the benzo ring of the naphthopyran (7-fluoro- or 9-fluoro-substitution) can provide naphthopyrans with color density, rapid response rates and balanced color absorption.

In graphic formula I, the general R groups may be independently selected from hydrogen, hydroxy, halogen (e.g., fluoro, bromo, chloro or iodo), alkyl group, alkoxy group, aryl group, carboxyester (e.g., C1-C4 ester of a C1-C4 alkyl), cyclo group, —CH(V)$R_{14}$, wherein V is —CN or —COOR$_{15}$, and each $R_{15}$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl groups, or the unsubstituted, mono- or di-substituted aryl groups phenyl or naphthyl, or the general R groups may be further independently selected from the group, —CH($R_{16}$)Y, wherein $R_{16}$ is hydrogen, $C_1$–$C_6$ alkyl or the unsubstituted, mono- or di-substituted aryl groups phenyl or naphthyl groups, and Y is —COOR$_{15}$, —COR$_{17}$, or —CH$_2$OR$_{18}$, wherein $R_{17}$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$) alkylamino, e.g. dimethyl amino, methyl propyl amino, etc., phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, i.e., (each phenyl group has one or two $C_1$–$C_6$ alkyl substituents, mono- or di-($C_1$–$C_6$)alkoxy substituted diphenylamino, morpholino, or piperidino; $R_{18}$ is hydrogen, —COR$_{15}$, $C_1$–$C_6$ alkyl, $C_1$–$C_3$ alkoxy($C_1$–$C_6$) alkyl, phenyl($C_1$–$C_3$)alkyl, mono($C_1$–$C_6$)alkyl group substituted phenyl($C_1$–$C_3$)alkyl group, mono($C_1$–$C_6$)alkoxy substituted phenyl($C_1$–$C_3$)alkyl groups, or the unsubstituted, mono- or di-substituted aryl groups phenyl or naphthyl groups, each of all of the afore described aryl group substituents being $C_1$–$C_6$ alkyl groups or $C_1$–$C_6$ alkoxy groups. Alternatively, any adjacent general R groups may together form a ring group, whether aromatic or non-aromatic, heterocyclic or carbocyclic. Preferably, $R_1$ is hydrogen, hydroxy, halogen (especially chloro), alkyl group of 1–5 carbon atoms, alkoxy groups of 1–5 carbon atoms, or aryl groups (particularly phenyl groups. $R_{14}$ may be any aliphatic or aromatic group, such as alkyl, substituted alkyl (e.g., substituted with halogen, hydroxy, alkoxy, etc.), end-group substituted alkyl, mid-group substituted alkyl, phenyl, substituted phenyl (e.g., substituted with alkyl, alkoxy, halogen, etc.) and the like.

More preferably, the general R groups are independently hydrogen, hydroxy, methyl, ethyl, methoxy, ethoxy, methoxymethyl, methylol, ethylol or chloro, except that in a preferred practice of the invention at least one of $R_1$ and $R_2$ comprise a cyclic ring with a nitrogen atom in the ring, and particularly at least one comprises a cyclic ring with a ring nitrogen bonded directly to the $R_1$ and $R_2$ positions. This practice of that aspect of the invention is more particularly described in copending U.S. patent application Ser. No. 09/224,004, filed on Dec. 31, 1998, now U.S. Pat. No. 6,478,988, titled "PHOTOCHROMIC SUBSTITUTED NAPHTHOPYRAN COMPOUNDS" in the name of Frank J. Hughes et al. According to that application, which is incorporated herein by reference, a novel compound comprising a photochromic naphthopyran comprising a 3,3-[substituted]-naphtho[2,1-b]pyran or a 2,2-[substituted]-naphtho[1,2-b] wherein:

a) one 3-position substituent on a 3,3-[substituted]-naphtho[2,1-b]pyran comprises a phenyl group (substituted or not) or b) one 2-position on a 2,2-[substituted]-naphtho[1,2-b] pyran comprises a phenyl group (substituted or not) and another of the 3-positions on the 3,3-[substituted]-naphtha [2,1-b]pyran or another of the 2-positions on the 3,3-[substituted]-naphtha[1,2-b]pyran comprises a substituted phenyl group having a substituent on the substituted phenyl group selected from the group consisting of an anthranilyl, azepinyl, benzoxazolyl, diazepinyl, diazolyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrrol, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinocyclidinyl, quinolyl, thiazolyl, triazolyl and triazyl groups. Therefore, at least one substituent on the phenyl groups attached at the 2-position of the benzopyran, as between $R_1$ and $R_2$ groups comprises an anthranilyl, azepinyl, benzoxazolyl, dialkylamino, diazepinyl, diazolyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrrol, isoquinolyl, isothiazolyl, julolideno, morpholino, morpholinyl, oxadiazolyl, oxathiazolyl, oxathiazyl, oxathiolyl, oxatriazolyl, oxazolyl, piperazinyl, piperazyl, piperidyl, puridazyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinocyclidinyl, quinolyl, thiazolyl, triazolyl or triazyl group. It is preferred that one of the phenyl groups attached at the 2-position of the benzopyran is unsubstituted, while the other phenyl group has the nitrogen containing ring.

In a less preferred embodiment of the invention, the $R_1$ and $R_2$ substituents in graphic formula I may each be selected from the group consisting of: (i) the unsubstituted, mono-, di-, and tri-substituted aryl groups, phenyl and naphthyl; (ii) the unsubstituted, mono- and di-substituted aromatic heterocyclic groups pyridyl, furanyl, benzofuran-2-yl, benzofuran-3-yl, thienyl, benzothien-2-yl and benzothien-3-yl, each of said aryl and aromatic heterocyclic substituents in parts (i) and (ii) being selected from the group consisting of hydroxy, amino, mono($C_1$–$C_6$)alkylamino, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, chloro and fluoro.

Where the term "group" is used to modify a chemical material (as in alkyl group), it is mean that the chemical material may be substituted or not, as is well understood by the ordinarily skilled organic chemist. For example, with respect to the term "alkyl group," that phrase includes not only pure hydrocarbon alkyl groups (e.g., $CH_3(CH_2)_n$—), but also alkyl groups substituted with conventional substituents that are compatible with the general use of those materials, such as hydroxy substitution, halogen substitution, ether linking groups, thioether linking groups, cyano groups, phenyl groups, and the like. Similarly, the terminology "phenyl group" allows for substitution on the phenyl ring with substituents that are common within the field of practice, such as alkyl groups, alkoxy groups, halogen groups, carboxy groups, and the like.

Compounds represented by graphic formula I described hereinbefore, may be prepared by the following described Reactions A through D. Methods for the preparation of compounds represented by graphic formula I and including the substituents $R_1$ and $R_2$, described hereinbefore, may be prepared by the following Friedel-Crafts Reaction. Compounds representative of the reagents are either purchased or prepared by Friedel-Crafts methods shown in Reaction A using an appropriately substituted or unsubstituted benzoyl chloride with a commercially available substituted or unsubstituted benzene compound. See the publication Friedel-Crafts and Related Reactions, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, reagent compounds are dissolved in a solvent, such as carbon disulfide or methylene chloride, and reacted in the presence of a Lewis acid, aluminum chloride.

In Reaction B, the substituted or unsubstituted ketone reagent is reacted with lithium acetylide or ethynyl magnesium bromide in a suitable solvent, such as anhydrous tetrahydrofuran (THF), to form the corresponding propargyl alcohol. Propargyl alcohols having groups on the 2-position of the benzopyran other than substituted and unsubstituted phenyl may be prepared from commercially available ketones or ketones prepared via reaction of an acyl halide with a substituted or unsubstituted benzene, naphthalene or heteroaromatic compound. Propargyl alcohols may be prepared by the methods described in U.S. Pat. No. 5,274,132, column 2, lines 40 to 68.

The present invention is more particularly described in the following examples which are intended as illustrative only, since numerous modifications and variations therein will be apparent to those skilled in the art.

These compounds can be prepared by a modified Claisen rearrangement as described in our above copending patent application, by reacting the appropriate phenol with a propargyl alcohol derivative. This modified Claisen rearrangement provides a general procedure for the preparation of pyran compounds, comprising heating a phenol with an appropriate propargyl derivative in a solvent in the presence of a suitable catalyst under mild reaction conditions. In contrast with reaction conditions normally employed in Claisen rearrangements, the process is carried out at relatively low temperatures, e.g. in boiling xylene or toluene and in the presence of a suitable catalyst. Generally, the reaction temperature should not exceed about 180° C. and is preferably not more than 160° C. or less. The reaction can be expressed in general terms as follows in which any phenol and a propargyl alcohol or propargyl alcohol derivative, such as a propargyl acetate are reacted. The reaction is catalysed by alumina and proceeds at relatively low temperatures with a marked absence of side reactions. In place of the acetate it is possible to use any aliphatic or aromatic carboxylate, e.g. the propionate or benzoate.

Improved yields are obtained using a propargyl acetate and heating this with a phenol in a solvent such as xylene in the presence of acidic alumina as catalyst. Surprisingly, these relatively mild conditions bring about a Claisen rearrangement whereas the traditional reaction conditions, e.g. seating to about 210° C. in strongly acid or base conditions, caused thermal decompositions of the reactants and/or desired product.

This process provides a convenient one-step synthesis of benzo- and naphthopyrans using any phenol and the appropriate propargyl alcohol or acetate or other propargyl alcohol derivative. Propargyl acetates can be prepared by reacting an appropriate ketone with lithium acetylide. A lithium acetylide/ethylene diamine complex is added with stirring to a solution of the ketone in a suitable solvent, such as tetrahydrofuran or dimethyl sulphoxide. The product is the corresponding propargyl alcohol and the alcohol is conveniently converted to the acetate by reaction with acetyl chloride in a suitable solvent.

However, because of the difficulty in effecting an efficient conversion of the propargyl alcohol to the acetate and the subsequent separation of the latter, it is desirable to utilize the propargyl alcohol directly as a starting material. The propargyl alcohol may be obtained by treating a ketone (which is substituted with a nitrogen-containing group in the ortho- or para- position) with a lithium acetylide/ethylene diamine complex or ethynyl magnesiumbromide in a suitable solvent such as ether.

In Reaction C for making the naphthols used in this invention, a substituted or unsubstituted benzophenone reagent is reacted with an ester of succinic acid such as dimethyl succinate reagent. Addition of the reactants to a solvent, e.g., toluene, containing potassium t-butoxide or sodium hydride as the base yields the Stobbe condensation half ester on the benzophenone are not identical, i.e., not structurally symmetrical, a mixture of cis and trans half esters will be formed that will require further purification to isolate a distinct isomer. The half ester undergoes cyclodehydration in the presence of acetic anhydride to form the acetoxynaphthalene. This product is reduced by common reducing agents, such as lithium aluminum hydride (LAH) or di-isobutyl aluminum hydride (DIBAL-H) to form the desired 1-naphthol.

In Reaction E, further methods for preparing naphthol compounds having a variety of general $R_5$ group substituents are described. Starting with certain reagent compounds, treatment with an alpha-bromoester in the presence of activated zinc dust results in additional naphthols. This reaction, referred to as the Reformatsky Reaction, is reviewed by R. L. Shriner in Organic Reactions Vol. 1, pp 1–37, 1942. These naphthol compounds can be further reacted with chlorinating reagents, for example thionyl chloride, to produce chlorinated derivatives. The compounds may also be dehydrohalogenated by heating in the presence of a tertiary amine, for example collidine, to yield alpha-, beta-unsaturated esters. Alternatively these compounds can be condensed with a compound containing an active methylene in the presence of an amine to produce alternative naphthopyran compounds. This reaction, referred to as the Knoevenagel Condensation, is reviewed by G. Jones in Organic Reactions Vol. 15, pp 204–599, 1967. Furthermore, the methylol containing naphthols may be etherified to give methyl ether derivatives.

The compounds used in the practice of the present invention may be used in those applications in which organic photochromic substances may be employed, such as optical lenses, e.g., vision correcting ophthalmic lenses and piano lenses, laminates for application of photochromic layers to surfaces, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans of the invention exhibit color changes from colorless to colors ranging from orange to blue/gray, and can provide blue colors with essentially a single wavelength range of major absorption.

Examples of contemplated naphthopyran compounds within the scope of the invention are the following:

(a) 2-(4-methoxyphenyl-2-(4-pyrrolidinophenyl)-5-methoxycarbonyl-6-methyl-7-fluoro-9-methoxy-[2H]-naphtho[1,2-b]pyran;

(b) 2-(4-methoxyphenyl)-2-(4-pyrrolidinophenyl)-5-methylol-6-methyl-7-fluoro-9-methoxy-[2H]-naphtho[1,2-b]pyran;

(c) 2-(4-methoxyphenyl)-2-(4-pyrrolidinophenyl)-5-methoxymethyl-6-methyl-7-fluoro-9-methoxy-[2H]-naphthol[1,2b]pyran;

(d) 2-(4-methoxyphenyl)-2-(4-pyrrolidinophenyl)-5-methoxycarbonyl-7-fluoro-9-methoxy-[2H]-naphthol[1,2-b]pyran;

(e) 2-(4-methoxyphenyl)-2-(4-pyrrolidinophenyl)-5-methylol-7-fluoro-9-methoxy-[2H]-naphthol[1,2-b]pyran;

(f) 2-(4-methoxyphenyl)-2-(4-pyrrolidinophenyl)-5-methoxymethyl-7-methoxy-9-fluoro-[2H]-naphtho[1,2-b]pyran;

(g) 2-(4-methoxyphenyl)-2-(4-pyrrolidinophenyl)-5-formyl-7-fluoro-9-methoxy-[2H]-naphtho[1,2-b]pyran.

(h) 2-(4-methoxyphenyl)-2-(4-pyrrolidinophenyl)-5-methyl-7-fluoro-9-methoxy-[2H]-naphtho[1,2-b]pyran; and (i) 2-(4-methoxyphenyl)-2-(4-(N,N-dimethylamino)phenyl)-5-methylol-7-fluoro-9-methoxy-[2H]-naphtho[1,2-b]pyran.

It is Contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro (indoline)benzopyrans, spiro(indoline)naphthopyrans, spiro (indoline)quinopyrans, spiro(indoline)pyrans, spiro (indoline)naphthoxazines, spiro(indoline) pyridobenzoxazines, spiro(benzindoline) pyridobenzoxazines, spiro(benzindoline)naphthoxazines, spiro(indoline)-benzoxazines, spiro(indoleno)benzoxazines, spiro(indoleno)benzopyrans, and mixtures of such photochromic compounds.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of Principles of Color Technology, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0–280 to 0.400 following activation to 4C percent luminous transmission by exposure to solar radiation (Air Mass 1 or 2).

The amount of photochromic compound containing that compound applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substance is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate)monomers, diethylene glycol dimethacrylate monomers, diisopropenyl benzene monomers, ethoxylated bisphenol A dimethacrylate monomers, ethylene glycol bismethacrylate monomers, poly (ethylene glycol)bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly(C.sub. 1-C.sub. 12 alkyl methacrylates), such as poly (methyl methacrylate), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate)monomers, e.g., diethylene glycol bis(allyl carbonate), and acrylate monomers. Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; polymerizates of a polyol(allyl carbonate) monomer, especially diethylene glycol bis(allyl carbonate), which monomer is sold under the trademark CR-39, and polymerizates of copolymers of a polyol(allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLES

Example 1

2,2-(4-methoxy-4'-pyrrolidino)diphenyl-5-methoxycarbonyl-6-methyl-7-fluoro-9-methoxy-[2H]-naphtho-[1,2-b]pyran Step I—Stobbe Condensation To a suspension of 3.7 g (33 mmol) of potassium t-butoxide in 60 ml of anhydrous toluene was added 5 g (30 mmol) of (2-fluoro-4-methoxy)acetophenone and 8 g (60 ml) of dimethyl succinate. The mixture was refluxed under a $N_2$ blanket for 30 minutes to yield a thick yellow 'mud.' The mixture was then cooled and treated with 45 ml of 1N HCl solution to give two phases, an organic phase and an aqueous phase. The organic phase was washed three times with separate 20 ml portions of water. The combined aqueous phase was extracted with ether. The ether extracts were then combined with the original organic phase, and then washed six time with separate 30 ml portions of 5% $Na_2CO_3$ solution. These washings were combined, acidified, and the 1 berated oily (brown semi-solid) half ester product was taken up in ether and dried over $MgSO_4$. Evaporation of the solvent gave 7 grams of yellow-brown oil which crystallized to a yellow solid on sitting.

Step II—Cyclization of Crude Stobbe Condensation Product (Half-Ester)

A solution of 6 g (21 mmol) of the half-ester prepared in Step I and 3.5 g (43 mmol) anhydrous sodium acetate in 30 ml of acetic anhydride was refluxed four 4 hours. Solvent was removed under reduced pressure. The residue was extracted with three separate portions of 30 ml of ether. The eftover was treated with 50 ml of 5% $Na_2CO_3$ solution, and extracted with three separate 30 ml portions of ethyl acetate. The combined organic phase was dried over $MgSO_4$ and evaporated to give 4.5 grams of dark, crude product.

Step III—Transesterification of the Cyclized Half-Ester 4.5 grams of the crude cyclization half-ester product was provided as a solution in 20 ml of methanol. Four (4) drops of concentrated hydrochloric acid was added to the half-ester solution and efluxed for 4 hours. The reaction was tracked by thin layer chromatography (silica, ethyl acetate/hexane=1:1). After a standard work-up (water-wash, ethyl acetate extraction), the second crude was run through a silica column with ethyl acetate/hexane 1:5). A tan colored powder 1-naphthol product weighing 0.5 grams was obtained.

Step IV—Pyran Formation from the Naphthol and a Propargyl Alcohol

To a solution of 0.5 g (1.9 mmol) of 3-carbomethoxy-4-methyl-5-fluoro-7-methoxy-1-naphthol and 1.2 grams (4mmol) of 1,1-(4-methoxy-4'-pyrrolidino)diphenyl propargyl alcohol in 20 ml of anhydrous toluene was added 0.5 g of chloroacetic acid. The reaction solution was refluxed for 3 hours and checked with TLC (silica, ethyl acetate/hexane 1:5). After standard work-up (water wash., separation, $MgSO_4$, dry, and evaporation). The resulting third crude was run through an alumina column with ethyl acetate/hexane (1:5) as the eluant. The photochromic naphthopyran was dried and washed with acetone (or ethyl acetate) to yield 150 mg of the light yellow colored powder dye. The dye showed two absorption peaks (at 590 nm and 490 nm) and turned to a blue color when stimulated by 365 nm UV radiation, and displayed a half time (extinction) of 5 seconds. (Structure No. 4 in the accompanying Formulae).

Example 2

2,2-(4-methoxy-4'-pyrrolidino)diphenyl-5-methlol-7-fluoro-9-methoxy-[2H]-naphtho-[1,2-b]pyran To a solution of 5 grams of methyl-(4-acetoxy-6-methoxy-8-fluoronaphthalene)-2-carboxylate, obtained by following Steps 1 and 2 in Example 1 where (2-fluoro-4-methoxy)aldehyde was used in the place of (2-fluoro-4-methoxy)acetophenone, in 150 ml of toluene was slowly charged 100 ml of diisobutylaluminium hydride in cyclohexane. The solution was allowed to stir at room temperature for 1 hour, and the reaction was ended by carefully charging 7.5 ml of water. The react on mix was filtered, and the solid was extracted with ethyl acetate. The combined organic phase was then concentrated and 1.7 grams of the product, 3-methylol-5-fluoro-7-methoxy-1-naphthol, precipitated out.

To a solution of 1.1 grams of the above naphthol and 2.1 grams of 1,1-(4-methoxy-4'-pyrrolidino)diphenyl propargyl alcohol in 50 ml of toluene, catalytic amount of chloroacetic acid was charged. The solution was refluxed for 1.5 hours, followed by neutralization with sodium carbonate and water wash. The Organic phase was concentrated and run through a silica column with hexane/ethyl acetate 4:1 as eluent. 325 mg of the desired product was obtained. (Structure No.3 in the accompanying formulae).

Example 3

Two other dyes, the structures of all are shown as Structures 1 and 2 in the accompanying formulae were also provided by essentially the identical procedures described above, by selection of the appropriate naphthol and propargyl alcohol. Each dye displayed photochromic behavior with two maximum peaks between 450 and 620 nm. It is a preferred characteristic of the dyes of the present invention to display two absorption maximum peaks, one between 440 and 510 nm, the other between 550 and 630 nm.

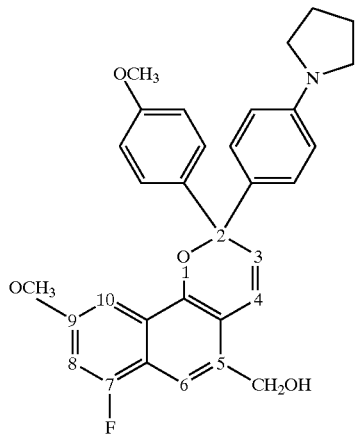

1

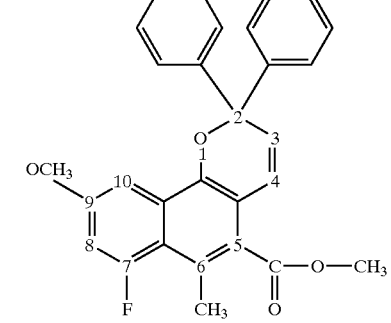

2

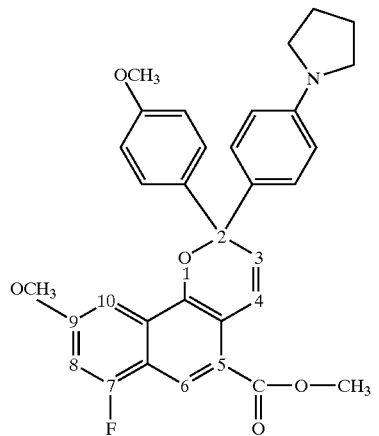

3

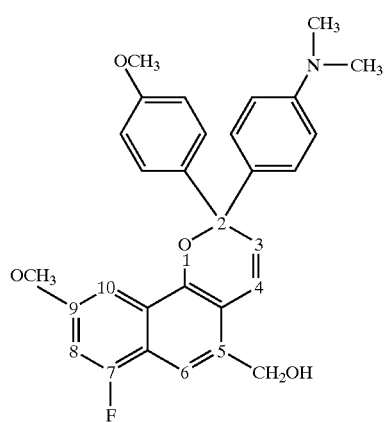

4

What is claimed:

1. A naphthopyran comprising 2,2-(4-methoxy-4'-pyrrolidino)diphenyl-5-methylol-7-fluoro-9-methoxy-[2H]-naphtho[1,2-b]pyran.

2. A photochromic composition containing at least one photochromic naphthopyran compound according to claim 1 and a polymeric host material selected from the group consisting of polycarbonates and polyvinyl alcohol.

3. A photochromic article having a layer thereon comprising the photochromic composition according to claim 2 characterized that the article is an ophthalmic lens.

\* \* \* \* \*